(12) United States Patent
Palepu

(10) Patent No.: US 7,429,390 B2
(45) Date of Patent: Sep. 30, 2008

(54) STABLE PHARMACEUTICAL COMPOSITIONS, PROCESSES FOR MAKING THE SAME AND METHODS OF THEIR USE

(76) Inventor: Nagesh R. Palepu, 30 Addis Dr., Southampton, PA (US) 18966-1166

( * ) Notice: Subject to any disclaimer, the term of this patent is extended or adjusted under 35 U.S.C. 154(b) by 0 days.

(21) Appl. No.: 11/743,262

(22) Filed: May 2, 2007

(65) Prior Publication Data

US 2007/0190085 A1   Aug. 16, 2007

(51) Int. Cl.
*A61K 9/00* (2006.01)
*A61K 47/00* (2006.01)
*A01N 43/04* (2006.01)

(52) U.S. Cl. .................. 424/400; 424/51; 424/439; 514/471; 514/653; 514/23

(58) Field of Classification Search ............. 514/471, 514/653, 23; 424/400, 51, 439
See application file for complete search history.

(56) References Cited

U.S. PATENT DOCUMENTS

| | | | |
|---|---|---|---|
| 4,585,790 A * | 4/1986 | Padfield et al. ............ 514/471 |
| 5,458,879 A | 10/1995 | Singh et al. |
| 5,881,926 A | 3/1999 | Ross |
| 6,383,471 B1 | 5/2002 | Chen et al. |
| 2003/0017189 A1 | 1/2003 | Wong et al. |
| 2004/0013693 A1 | 1/2004 | Bobotas et al. |
| 2006/0100271 A1 | 5/2006 | Whitehead |
| 2006/0165807 A1 | 7/2006 | Castan et al. |

FOREIGN PATENT DOCUMENTS

| | | |
|---|---|---|
| WO | WO 93/09775 | 5/1993 |
| WO | WO 95/10274 A1 | 4/1995 |
| WO | WO 99/04788 | 2/1999 |
| WO | WO 99/62498 A1 | 12/1999 |
| WO | WO 01/056547 A2 | 8/2001 |

OTHER PUBLICATIONS

Stewart, James T., et al., "Stability of Ranitidine in Intravenous Admixtures Stored Frozen, Refrigerated, and at Room Temperature". American Journal of Hospital Pharmacy (US), vol. 47(9), Sep. 1990, pp. 2043-6.

Galante, Leonard J., et al., "Stability of Ranitidine Hydrochloride at Dilute Concentration in Intravenous Infusion Fluids at Room Temperatute". American Journal of Hospital Pharmacy (US) vol. 47(7), Jul. 1990, pp. 1580-5.

Williams, Melissa, et al., "In Vitro Evaluation of the Stability of Ranitidine Hydrochloride in Total Parenteral Nutrient Mixtures". American Journal of Hospital Pharmacy (US), vol. 47(7), Jul. 1990, pp. 1574-9.

* cited by examiner

*Primary Examiner*—Mina Haghighatian
(74) *Attorney, Agent, or Firm*—Blank Rome LLP

(57) ABSTRACT

The present invention is generally related to alcohol free, liquid ranitidine formulations for oral administration. In particular, the present invention is related to stable, syrup formulations having ranitidine as an active ingredient for oral administration, processes for making the same, and methods of their use. The ranitidine of the present invention is stable in non-polar media or media having a relatively low polarity such that the dielectric constant is less than about 60, and is achieved by using certain saccharides, certain relatively high molecular weight starches, and/or certain celluloses instead of alcohol.

20 Claims, No Drawings

STABLE PHARMACEUTICAL COMPOSITIONS, PROCESSES FOR MAKING THE SAME AND METHODS OF THEIR USE

FIELD OF THE INVENTION

The present invention is generally related to alcohol free, liquid ranitidine formulations for oral administration. In particular, the present invention is related to stable, syrup formulations having ranitidine as an active ingredient for oral administration, processes for making the same, and methods of their use.

BACKGROUND OF THE INVENTION

Ranitidine [N-[2-[[[5-(dimethylamino)methyl-2-furanyl]methyl]thio]ethyl]-N'-methyl-2-nitro-1, 1-ethenediamine] and physiologically acceptable salts thereof (having, for example, the empirical formula $C_{13}H_{22}N_4O_3S$—HCl and the structural Formula I shown below) are disclosed in British Patent Specification No. 1565966.

Formula I:

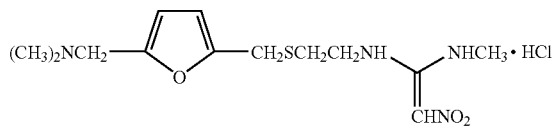

According to current prescribing information, the compound of Formula I is indicated for short-term treatment of active duodenal ulcer (most patients found to heal within 4 weeks; studies available have not assessed the safety of ranitidine in uncomplicated duodenal ulcer for periods of more than 8 weeks); maintenance therapy for duodenal ulcer patients at reduced dosage after healing of acute ulcers (no placebo-controlled comparative studies have been carried out for periods of longer than 1 year); the treatment of pathological hypersecretory conditions (e.g., Zollinger-Ellison syndrome and systemic mastocytosis); short-term treatment of active, benign gastric ulcer (most patients found to heal within 6 weeks; the usefulness of further treatment has not been demonstrated; studies available have not assessed the safety of ranitidine in uncomplicated, benign gastric ulcer for periods of more than 6 weeks); maintenance therapy for gastric ulcer patients at reduced dosage after healing for acute ulcers (placebo-controlled studies have been carried out for 1 year); treatment of GERD (symptomatic relief found to commonly occurs within 24 hours after starting therapy with 150 mg b.i.d.); treatment of endoscopically diagnosed erosive esophagitis (symptomatic relief of heartburn found to commonly occur within 24 hours of therapy initiation with 150 mg b.i.d.); and maintenance of healing of erosive esophagitis (placebo-controlled trials have been carried out for 48 weeks).

Many of the formulations containing the compound of Formula I disclosed in British Patent Specification No. 1565966 are known to be unstable and, therefore, not appropriate for marketable formulations that are required to be stable. U.S. Pat. No. 4,585,790, on the other hand, discloses improved aqueous formulations of ranitidine that are more stable. That patent discloses ranitidine formulations having a pH in the range 6.5 to 7.5 that are suitable formulations for injections for intravenous and intramuscular administration, continuous infusions, and oral preparations such as syrups. Similarly, U.S. Pat. No. 5,068,249 discloses stabile, aqueous formulations of ranitidine containing ethanol as a stabilizer. That patent describes a pharmaceutical composition which is an aqueous formulation of ranitidine and/or one or more physiologically acceptable salts thereof containing ethanol and that is suitable for administration to patients and will, in general, contain at least one conventional pharmaceutical excipient in addition to the ethanol and ranitidine and/or physiologically acceptable salts thereof.

U.S. Pat. No. 6,265,449 discloses an aqueous pharmaceutical composition for oral administration comprising ranitidine, or a pharmaceutically acceptable salt thereof, that contains alcohol and low color, metal, turbidity (LCMT) sucrose, which was found to improved stability, bioavailability and taste-masking of ranitidine while allowing the volume of the alcohol required in the solution to be reduced.

A commercially available version of a stable pharmaceutically acceptable salt form of the compound of Formula I is known as ZANTAC® syrup, which is described in prescribing information as being a clear peppermint-flavored liquid that contains 16.8 mg of ranitidine-HCl equivalent to 15 milligrams (mg) of ranitidine per 1 milliliter (ml) (75 mg/5 mL) in bottles of 16 fluid ounces (one pint). Because of its relative instability, ZANTAC® is usually stored between about 4° and about 25° C. (39° and 77° F.) in tight, light-resistant containers.

SUMMARY OF THE INVENTION

It has been surprisingly found that aqueous syrup formulations containing the compound of Formula I, or other physiologically acceptable salts of ranitidine, can be stabilized without the use of ethanol or other alcohols as taught in U.S. Pat. Nos. 5,068,249 and 6,265,449, and at pH ranges that are higher and lower than the ranges set forth in those patents. In particular, it has been found that ranitidine is stable in non-polar media or media having a relatively low polarity such that the dielectric constant is less than about 60, the stability achieved by using certain saccharides, starches (preferably relatively high molecular weight starches), and/or certain celluloses instead of alcohol; buffers may or may not be needed.

An advantage of the formulations of the present invention is the relatively high concentration of the saccharides that help mask the taste of ranitidine.

Another advantage of the formulations of the present invention is that non-alcoholic aqueous formulations are generally preferred by, among others, parents who administer those formulations to their children.

Thus, the present invention involves a pharmaceutical composition which is an aqueous formulation containing a pharmaceutically effective amount of ranitidine and/or one or more physiologically acceptable salts thereof for treatment of conditions mediated through histamine $H_2$-receptors, the formulation having a pH preferably within the range of about 4.85 to about 7.99, and most preferably within the range of about 6.5 to about 7.5, making it suitable for administration to humans and other mammals.

DETAILED DESCRIPTION OF THE INVENTION

The present invention involves a pharmaceutical composition of the compound of Formula I, or other physiologically acceptable salts of ranitidine, that is stable when dissolved in or combined with one or more saccharides, one or more starches (preferably relatively high molecular weight starches), and/or celluloses as stabilizers. In addition, physiologically acceptable carriers, excipients, diluents, colorants, flavorants, and other substances may also be added.

The preferred saccharides of the present invention include, but are not limited to, inverse sugar, dextrose, glucose, trehalose, lycasin (70% corn syrup), cyclodextrins, niacinamide, dextran, and other mono-, oligo- and poly-saccharides.

The preferred starches of the present invention include, but are not limited to, maize starch, potato starch, pregelatinized starch, topiaco and hydroxyl ethyl starch (HES). Cyclodextrins, which are cyclic carbohydrates derived from starch, are also contemplated as part of the invention for use in the stable compositions of ranitidine hydrochloride.

The preferred cellulose of the present invention include, but is not limited to, hydroxyl propyl cellulose (HPC), hydroxy propyl methyl cellulose (HPMC), and hydroxyl ethyl cellulose (HEC).

The concentration of the stabilizers preferably varies from about 5% to about 80% volume per total final composition, preferably from about 40% to about 70% volume per total final composition, most preferably about 5%, especially in the case of cellulose.

The concentration of the compound of Formula I is preferably about 16.8 mg/ml.

Stable pharmaceutical formulations of ranitidine hydrochloride using PVP and niacinamide are also contemplated.

Excipients include those that are suitable for the manufacture of aqueous suspensions and include, but are not limited to suspending agents, dispersing or wetting agents, preservatives, coloring agents, flavoring agents, and sweetening agents.

Stabilization of the ranitidine in the present invention is accomplished by, for example, reducing the dielectric constant of water. Water is a very polar medium and ranitidine, being a polar molecule, effectively degrades in water. By reducing the dielectric constant of the medium in which ranitidine will come in contact with, or by reducing the water activity at the reaction site, the stability of the ranitidine may be increased, which is to say that the degradation potential may be reduced.

The hydrolytic degradation reaction involving ranitidine is essentially as follows:

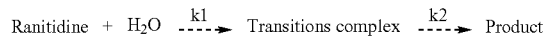

Previous attempts to affect the degradation of ranitidine formulations focused on slowing down the rate of conversion of the ranitidine transition complex (k2) to the final degradation product. In the present invention, the stabilizers preferably reacts with water and thus reduces the water activity at the reaction site. That, in turn, slows down the rate of formation of the transition complex (k1), which controls the overall degradation of the ranitidine.

It has been found that buffering may or may not be needed with the formulations of the present invention. If a buffer is used, the buffer can be, but is not limited to, acetate, citrate, phosphate, succinate, or any pharmaceutically acceptable acid or base with pKa ranging 4.5 to 6.5. The preferred buffer includes citric acid and disodium hydrogen orthophosphate, or potassium dihydrogen phosphate and disodium hydrogen phosphate.

Formulations of the present invention may be prepared by combining, in an appropriate sequence, an amount of the compound of Formula I, or other physiologically acceptable salts of ranitidine, with one or more saccharides or high molecular weight starches, and with one or more physiologically acceptable carriers, excipients, diluents, colorants, flavorants, or other substances, whereby the compound of Formula I is combined with the one or more saccharides or one or more high molecular weight starches, or one or more celluloses in order to achieve a generally stabilizing effect on the ranitidine. The resulting ranitidine concentration is about 15 mg/ml of free base (ranitidine plus water), preferably 16.8 mg/ml of free base.

The formulations of the invention may be made according to the following process. First, potable water, e.g. 40 mL, is transferred into a beaker calibrated to a predetermined batch volume, e.g. 50 ml. An amount of raniditine is added to the water to make a solution having a desired concentration, e.g. about 16.8 mg/ml. Into that solution, a sufficient amount of a buffer is dissolved to obtain a target pH, e.g. about 4.85 to about 7.99, preferably about 6.5 to about 7.5. Next, a stabilizer, such as one or more saccharides, and/or high molecular weight starches, and/or HPC or other cellulose, is/are admixed with the water/ranitidine/buffer solution in an amount necessary to stabilize the raniditine. An amount of potable water is then added to fill to the predetermined batch volume.

In addition to the above components, one or more excipients may be added to the solution along with the stabilizing agent.

Without further description, it is believed that one of ordinary skill in the art can, using the preceding description and the following illustrative examples, make and utilize the compounds of the present invention and practice the methods. The following examples are given to illustrate the present invention. It should be understood that the invention is not to be limited to the specific conditions or details described in these examples.

EXAMPLE 1

The formulations of the invention are made according to the following process. First, 40 ml of potable water are transferred into a beaker calibrated to a batch volume of 50 ml. An amount of ranitidine is added to the water to make a solution having a concentration of about 16.8 mg/ml. Into that solution, a sufficient amount of a buffer is dissolved to obtain desired pH. In some occasions. 0.1N NaOH was also used to adjust the pH in addition to buffer to get the target pH. Next, a stabilizing agent such as one or more saccharides and/or high molecular weight starches is/are admixed with the water/ranitidine/buffer solution in an amount necessary to stabilize the ranitidine. An amount of potable water is then added to create a batch volume of 50 ml. Samples of the resulting composition are introduced into 5-ml flint stopper vials for accelerated stability tests.

In addition to the above components, one or more excipients may be added to the solution along with the stabilizing agent.

EXAMPLE 2

Compositions and pharmaceutical compositions containing ranitidine hydrochloride are shown in Table 1 below.

TABLE 1

| LOT NO | FORMULATION | PH |
|---|---|---|
| RNT-2 (Control) | Drug- 16.8 mg/ml KH$_2$PO$_4$ 1.0 mg/ml | 6.81 |

TABLE 1-continued

| LOT NO | FORMULATION | PH |
|---|---|---|
| RNT-9 | $K_2HPO_4$ 2.4 mg/ml<br>Ethanol 7.5%<br>Water - q.s. to target volume<br>Drug 16.8 mg/ml,<br>Dextran- 10%<br>$KH_2PO_4$ 3.0 mg/ml<br>$K_2HPO_4$ 1.0 mg/ml<br>Corn syrup 16%<br>Water q.s. to target volume | 5.6 |
| RNT-10 | Drug 16.8,<br>Dextran- 10%<br>$KH_2PO_4$ 1.0 mg/ml<br>$K_2HPO_4$ 2.4 mg/ml<br>Corn syrup 16%<br>Water q.s. to target volume | 6.81 |
| RNT-11 | Drug 16.8 mg/ml<br>Dextran - 10%<br>Corn syrup 16%<br>$KH_2PO_4$ 1.0 mg/ml<br>$K_2HPO_4$ 2.4 mg/ml<br>pH adj. With 0.1N<br>Water q.s. to target volume | 7.85 |
| RNT-13 | Drug 16.8 mg/ml<br>HydroxyEthyl Starch 10%<br>Corn syrup 16%<br>$KH_2PO_4$ 1.0 mg/ml<br>$K_2HPO_4$ 2.4 mg/ml<br>pH adj. with 0.1N NaOH<br>Water q.s. to target volume | 7.02 |
| RNT-14 | Drug 16.8 mg/ml<br>Hydroxyethyl Starch - 10%<br>Corn syrup 16%<br>$KH_2PO_4$ 1.0 mg/ml<br>$K_2HPO_4$ 4.0 mg/ml<br>Water q.s. to target volume | 7.83 |
| RNT-20 | Drug 16.8 mg/ml<br>Alcohol 7.5% (v/v)<br>No pH adjustment<br>Water q.s. to target volume | 5.22 |
| RNT-21 | Drug 16.8 mg/ml<br>Alcohol 7.5% (v/v)<br>$KH_2PO_4$ 1.0 mg/ml<br>$K_2HPO_4$ 3.0 mg/ml<br>Water q.s. to target volume | 7.2 |

EXAMPLE 3

Eight pharmaceutical compositions containing ranitidine hydrochloride were prepared according to the formulations shown in Table 2. Two-week and/or four-week stability tests were conducted at 40° C. on each formulation with assays of ranitidine-HCl being conducted initially at the start of each test and at the end of the two week and/or four week test period. The results of the tests are shown in Table 2.

TABLE 2

| LOT NO | FORMULATION | PH | STABILITY ANALYSIS (ASSAY OF RANITIDINE HCL) | | |
|---|---|---|---|---|---|
| | | | INITIAL | 2 WKS AT 40° C. | 4 WKS AT 40° C. |
| RNT-12 | Drug 16.8 mg/ml<br>Starch 10%<br>corn syrup 16%<br>KH2PO4 3 mg/ml<br>Na2HPO4 1 mg/ml<br>Water qs to 1 ml | 5.6 | 100% | | 106% |
| RNT-14 | Drug 16.8 mg/ml<br>HES 10%<br>corn syrup 16%<br>KH2PO4 1 mg/ml<br>Na2HPO4 4 mg/ml<br>Water qs to 1 ml | 7.85 | 100% | | 102% |
| RNT-20 | Drug 16.8 mg/ml<br>Alcohol 7.5% (v/v)<br>No pH adustment<br>Water qs to target volume | 5.22 | 100 | 99 | 98 |
| RNT-21 | Drug 16.8 mg/ml<br>Alcohol 7.5% (v/v)<br>KH2PO4 1 mg/ml<br>Na2HPO4 3 mg/ml<br>Water qs to target volume | 7.2 | 100 | 99 | 96 |
| RNT-31 | Drug 16.8 mg/ml HPBCD 1.5 mg/ml<br>Niacinamide 3 mg/ml<br>pH adjusted with 0.1N NaoH | 7.99 | 100% | | 96% |
| RNT-32 | Drug 16.8 mg/ml<br>HPBCD 1.5 mg/ml<br>Niacinamide 3 mg/ml<br>HES 100 mg/ml<br>KH2PO4 3 mg/ml<br>Na2HPO4 1 mg/ml<br>Water qs to 1 ml | 5.5 | 100 | 98 | 97 |
| RNT-51 | Drug 16.8 mg/ml<br>Niacinamide 10 mg/ml<br>pH adjusted with 0.1N NaOH<br>Water qs to 1 ml | 7.83 | 100 | NP | 93 |
| RNT-53 | Drug 16.8 mg/ml<br>PVPK 10 mg/ml<br>KH2PO4 1 mg/ml<br>Na2HPO4 1 mg/ml<br>pH adjusted with 0.1N NaOH<br>Water qs to 1 ml | 7.84 | 100 | NP | 102 |

EXAMPLE 4

We have also formulated ranitidine with hyrdoxypropyl cellulose (HPC). Hydroxypropyl cellulose is used as a binder in the granulation step of tablet dosage form development. It has high affinity for water. Hence, it was theorized that the HPC is extensively hydrated by water thereby reduces the activity of water at the reaction site. A formulation, RNT-42, comprising ranitidine 16.8 mg/ml, hydroxypropyl cellulose 5%, $KH_2PO_4$ 3 mg/ml, $Na_2HPO_4$ 1 mg/ml., pH adjusted to 5.8 was prepared and its stability along with the simulated ranitidine syrup (innovator formulation) was evaluated. The samples ware assayed by the USP monograph method. The stability data is summarized in TABLE 4.

TABLE 4

STABILITY ASSAY OF RNT-42 at 40° C.

| DAYS | ASSAY (% of target) |
|---|---|
| INITIAL | 103% |
| 30 DAYS | 102% |

TABLE 4-continued

STABILITY ASSAY OF RNT-42 at 40° C.

| DAYS | ASSAY (% of target) |
|---|---|
| 60 DAYS | 103% |
| 90 DAYS | 99% |

Target: 16.8 mg/ml ranitidine HCl

The impurity samples were taken at different time periods and were assayed by using a HPLC method described under ranitidine monograph in Pharm. Eur. Impurities B, C, E and G are identified as know impurities in the monograph. RRT means relative retention time of degradation peaks with reference to ranitidine peak. The impurities are summarized in TABLES 5-6.

TABLE 5

IMPURITY AT 40° C. OF RNT-42

| DAYS | RRT | Area % | Area | Name of the impurity |
|---|---|---|---|---|
| 30 | 0.27 | 0.11 | 3010 | Unknown |
|  | 0.57 | 0.06 | 1690 | Unknown |
|  | 0.58 | 0.06 | 1794 | C |
|  | 0.62 | 0.13 | 3662 | Unknown |
|  | 0.85 | 0.17 | 4929 | Unknown |
| 60 | 0.28 | 0.10 | 2395 | Unknown |
|  | 0.55 | 0.21 | 4846 | Unknown |
|  | 0.60 | 0.09 | 2213 | C |
|  | 0.70 | 0.08 | 1775 | E |
|  | 0.86 | 0.44 | 10359 | Unknown |
|  | 1.16 | 0.16 | 3764 | Unknown |
| 90 | 0.22 | 0.20 | 4237 | Unknown |
|  | 0.28 | 0.13 | 2818 | Unknown |
|  | 0.50 | 0.14 | 2915 | B |
|  | 0.57 | 0.14 | 2942 | C |
|  | 0.82 | 0.51 | 10550 | Unknown |

TABLE 6

IMPURITY AT 25° C. OF RNT-42

| S.No. | DAYS | RRT | Area % | Area | Name of the Impurity |
|---|---|---|---|---|---|
| 1 | 90 | 0.22 | 0.057 | 1217 | Un known |
|  |  | 0.50 | 0.083 | 1795 | B |
|  |  | 0.57 | 0.090 | 1945 | C |

EXAMPLE 5

The following composition (RNT-57) was prepared and assayed for stability and impurity: drug (ranitidine), 2.5% HPC, 5% HES, niacinamide 1.5 mg/ml, cyclodextrin 1.5 mg/ml, and buffers (pH adjusted 5.7).

TABLE 7

STABILTIY ASSAY OF RNT-57

| DAYS | ASSAY (% of target) |
|---|---|
| INITIAL | 113 |
| 30 DAYS | 111 |
| 60 DAYS | 102 |

Target concentration: 16.8 mg/ml

TABLE 8

IMPURITY AT 40° C. OF RNT-57

| DAYS | RRT | Area % | Area | Name of the impurity |
|---|---|---|---|---|
| Initial | 0.28 | 0.09 | 2356 | Unknown |
|  | 0.60 | 0.07 | 1803 | C |
|  | 1.16 | 0.09 | 2350 | Unknown |
| 30 | 0.28 | 0.12 | 3039 | Unknown |
|  | 0.55 | 0.15 | 3795 | Unknown |
|  | 0.60 | 0.06 | 1570 | C |
|  | 0.86 | 0.26 | 6583 | Unknown |
|  | 1.16 | 1.16 | 3230 | Unknown |
| 60 | 0.12 | 1.24 | 29600 | Unknown |
|  | 0.18 | 2.74 | 65566 | G |
|  | 0.26 | 0.17 | 3985 | Unknown |
|  | 0.84 | 0.50 | 11944 | Unknown |

EXAMPLE 6

The following composition (RNT-58) was prepared and assayed for stability and impurity: drug, 2.5% HPC, 5% HES, niacinamide 1.5 mg/ml, cyclodextrin 1.5 mg/ml, and buffer (pH adjusted 7.9). RNT-58 is identical to RNT-57 in composition with exception that pH is adjusted to 7.9.

TABLE 9

STABILITY ASSAY OF RNT-58

| S.NO. | DAYS | ASSAY (%) |
|---|---|---|
| 1 | INITIAL | 101 |
| 2 | 30 DAYS | 101 |
| 3 | 60 DAYS | 89 |

TABLE 10

IMPURITY AT 40° C. OF RNT-58

| DAYS | RRT | Area % | Area | Name of the impurity |
|---|---|---|---|---|
| Initial | 0.28 | 0.06 | 1312 | Unknown |
|  | 0.60 | 0.06 | 1257 | C |
| 30 | 0.55 | 0.16 | 3753 | Unknown |
|  | 0.60 | 0.13 | 2919 | C |
|  | 0.85 | 0.34 | 7669 | Unknown |
|  | 1.16 | 0.07 | 1495 | Unknown |
| 60 | 0.20 | 4.35 | 113447 | G |
|  | 0.85 | 0.89 | 22818 | Unknown |

EXAMPLE 7

The following TABLES 10 and 11 compares the stability and impurities of the commercially available formulation (RNT-02) with RNT-42. RNT-02 is simulated version of commercially available formulation without flavor and preservatives. RNT-02 consists of the following ingredients:

| Ranitidine HCl: | 16.8 mg/ml |
|---|---|
| Ethyl alcohol: | 7.5% (v/v) |
| KH2PO4: | 1 mg/ml |
| K2HPO4: | 2.4 mg/ml |
| pH adjusted: | 7.0 |

TABLE 10

STABILITY COMPARISON

| Formulation | Potency 1 month (%) | Potency 2 months (%) | Potency 3 months (%) |
|---|---|---|---|
| RNT-42 Lead Formulation | 100 | 98 | 98 |
| Control RNT-02 | 100 | 97 | 96 |

TABLE 11

IMPURITY COMPARISON

| LOT# | 30 DAYS Related Substances | | | 60 DAYS Related Substances | | | 90 DAYS Related Substances | | |
|---|---|---|---|---|---|---|---|---|---|
| | Impurity | % Area | RRT | Impurity | % Area | RRT | Impurity | % Area | RRT |
| RNT-42 | Unknown | 0.11 | 0.28 | Unknown | 0.10 | 0.28 | Unknown | 0.20 | 0.22 |
| | Unknown | 0.06 | 0.57 | Unknown | 0.21 | 0.55 | Unknown | 0.13 | 0.28 |
| | Unknown | 0.06 | 0.58 | C | 0.09 | 0.60 | B | 0.14 | 0.50 |
| | C | 0.13 | 0.62 | E | 0.08 | 0.70 | C | 0.14 | 0.57 |
| | Unknown | 0.17 | 0.85 | Unknown | 0.44 | 0.86 | Unknown | 0.51 | 0.82 |
| | | | | Unknown | 0.16 | 1.16 | | | |
| | Total | 0.53 | | Total | 1.08 | | Total | 1.12 | |
| RNT-02 Control | Unknown | 0.33 | 0.33 | Unknown | 0.14 | 0.18 | Unknown | 0.49 | 0.55 |
| | C | 0.17 | 0.59 | Unknown | 0.17 | 0.44 | C | 0.47 | 0.60 |
| | Unknown | 0.33 | 0.81 | C | 0.29 | 0.59 | E | 0.13 | 0.70 |
| | | | | Unknown | 0.47 | 0.81 | Unknown | 0.86 | 0.86 |
| | Total | 0.83 | | Total | 1.07 | | Total | 1.95 | |

As shown above, the alcohol free formulation showed good stability at 40° C. as only 2% loss observed at over 3-month storage. Also, total impurities formed in the alcohol free formulation are lower than that of the simulated innovator formulation. Based on this data we can project a shelf life of 3 years under ambient storage conditions. There are quite a few impurities greater than 0.1%. However, the degradation products observed under accelerated conditions may not necessarily form under ambient storage condition. The stability at 3 months at 25° C. showed only one impurity peak.

EXAMPLE 8

The following composition (RNT-R1) was prepared and assayed for stability and impurity: drug 16.8 mg/mL and HPC 50.0 mg/mL (pH adjusted 5.73 with 0.1N sodium hydroxide).

TABLE 12

Stability of RNT-R1 at 40° C.

| TIME | STABILITY (%) | IMP. (%) | RRT | IMP. NAME | pH |
|---|---|---|---|---|---|
| Initial | 100 | Impurities not detected | | | 5.73 |
| 30 Days | 97.9 | 0.07 | 0.60 | C | 6.00 |
| | | 0.27 | 0.88 | UK | |
| | Total impurities | 0.34 | | | |
| 60 Days | 96.8 | 0.38 | 0.26 | UK | 6.32 |
| | | 0.14 | 0.55 | UK | |
| | | 0.18 | 0.60 | C | |
| | | 0.42 | 0.88 | UK | |
| | | 0.26 | 1.27 | UK | |
| | Total impurities | 1.38 | | | |
| 90 Days | 95.5 | 0.42 | 0.26 | UK | |
| | | 0.33 | 0.46 | UK | |
| | | 0.17 | 0.55 | UK | |
| | | 0.24 | 0.60 | C | |
| | | 0.54 | 0.88 | UK | |
| | | 0.14 | 1.24 | UK | |
| | Total impurities | 1.84 | | | |

UK—unknown
IMP—impurity

TABLE 13

Stability of RNT-R1 at 25° C.

| TIME (HRS) | STABILITY (%) | IMP. % | RRT | IMP. NAME | pH |
|---|---|---|---|---|---|
| INITIAL | 100.0 | NOT DETECTED | | | 5.73 |
| 90 DAYS | 99.1 | 0.04 | 0.88 | UK | 5.54 |
| 180 DAYS | 99.0 | 0.06 | 0.88 | UK | 5.82 |

The accelerated stability of RNT-R1 showed comparable impurity profile compared to the pilot formulation (RNT-42).

EXAMPLE 9

In the next study, we studied the stability of RNT-R1 in the presence of sweetener and preservative. The formulation composition and stability data presented below:

| Composition (RNT-R2) | |
| --- | --- |
| Drug: | 16.8 mg/ml |
| HPC: | 50.0 mg/ml |
| Sodium saccharin: | 3.0 mg/ml |
| Methylparaben-Na (MPS): | 0.7 mg/ml |
| Propylparaben-Na: (PPS): | 0.2 mg/ml |
| pH adjusted with 0.1N NaOH: | 5.69 |

TABLE 14

STABILITY AND IMPURITIES OF RNT-R2 AT 40° C.

| TIME (HRS) | STABILITY (%) | IMP. % | RRT | IMP NAME | pH |
| --- | --- | --- | --- | --- | --- |
| INITIAL | 100.0 | NOT DETECTED | | | 5.73 |
| 30 DAYS | 98.2 | 0.27 | 0.88 | UK | 6.01 |
| Total impurities | | 0.27 | | | |
| 60 DAYS | 97.1 | 0.19 | 0.27 | UK | 6.33 |
| | | 0.23 | 0.45 | UK | |
| | | 0.52 | 0.88 | UK | |
| Total impurities | | 0.94 | | | |
| 90 DAYS | 96.4 | 0.23 | 0.26 | UK | 6.32 |
| | | 0.17 | 0.45 | UK | |
| | | 0.69 | 0.88 | UK | |
| Total impurities | | 1.09 | | | |

The stability of RNT-R2 appears to be better than that of RNT-R1. The number of impurity peaks limited to three and total peak are is around 1.1% compared to 1.84% for the RNT-R1. The pH of the syrup at the end of 3 months is also below 6.5.

TABLE 15

STABILITY AND IMPURITIES OF RNT-R2 AT 25° C.

| TIME (HRS) | STABILITY (%) | IMP. % | RRT | IMP NAME | pH |
| --- | --- | --- | --- | --- | --- |
| INITIAL | 100.0 | IMPURITIES NOT DETECTED | | | 5.73 |
| 90 Days | 99.0 | 0.05 | 0.83 | UK | 6.01 |
| 180 Days | 99 | 0.07 | 0.83 | UK | 6.26 |

EXAMPLE 10

In the next set of experiment, we tested the stability of RNT-R2 in the presence of buffer at pH 7.8. The purpose of this experiment is to determine the effect of weakly alkaline pH condition on the stability of ranitidine. The composition (RNT-R3) and the stability is presented below.

Composition (RNT-R3):

| Drug | 16.8 mg/ml |
| --- | --- |
| HPC | 50.0 mg/ml |
| $KH_2PO_4$ | 1.0 mg/ml |
| $Na_2HPO_4$ | 4.0 mg/ml |
| Sodium Saccharin | 3.0 mg/ml |
| MPS | 0.7 mg/ml |
| PPS | 0.2 mg/ml |
| pH | 7.79 |

TABLE 16

STABILITY AND IMPURITIES OF RNT-R3 AT 40° C.

| TIME (HRS) | ASSAY (%) | IMP. % | RRT | IMP NAME | pH |
| --- | --- | --- | --- | --- | --- |
| INITIAL | 100.0 | Impurities not detected | | | 7.84 |
| 30 Days | 96.9 | 0.35 | 0.58 | C | 7.78 |
| | | 0.31 | 0.88 | J | |
| Total Impurities | | 0.66 | | | |
| 60 Days | 94.2 | 0.12 | 0.11 | H | 7.42 |
| | | 0.06 | 0.53 | UK | |
| | | 0.18 | 0.56 | UK | |
| | | 0.12 | 0.72 | E | |
| | | 0.68 | 0.83 | UK | |
| | | 0.08 | 1.27 | UK | |
| | | 0.30 | 1.32 | I | |
| | | 0.40 | 1.61 | UK | |
| | | 0.39 | 1.69 | A | |
| Total Impurities | | 2.33 | | | |
| 90 Days | 91.3 | 0.16 | 0.11 | H | 7.45 |
| | | 0.05 | 0.51 | B | |
| | | 0.21 | 0.55 | UK | |
| | | 0.13 | 0.72 | E | |
| | | 0.83 | 0.83 | UK | |
| | | 0.31 | 1.27 | UK | |
| | | 0.40 | 1.35 | UK | |
| | | 0.25 | 1.64 | UK | |
| Total Impurities | | 2.34 | | | |

As shown in the table, the alkaline conditions have adverse effect on the stability of ranitidine syrup and also observed late eluting degradation products.

TABLE 17

STABILITY OF RNT-R3 AT 25° C.

| TIME (HRS) | ASSAY (%) | IMP. % | RRT | IMP NAME | pH |
| --- | --- | --- | --- | --- | --- |
| INITIAL | 100.0 | NOT DETECTED | | | 7.84 |
| 90 DAYS | 97.1 | 0.04 | 0.83 | UK | 7.41 |
| | | 0.08 | 1.65 | UK | |
| TOTAL IMPURITES | | 0.12 | | | |

Even at room temperature we observed 3% degradation suggesting that the HPC containing ranitidine syrup is not as stable under neutral to weakly alkaline conditions. The HPC containing formulation showed better stability under weakly acidic condition.

EXAMPLE 11

In the next set of experiments we studied the stability of RHT-R2 in the presence Xylitol (RNT-R5) and Xylitol plus flavoring agent (mint oil) (RNT-R6). We have conducted these trials in triplicate, i.e., three batches were made per lot. The data presented here is the mean of the three batches. The syrup was stored in PET bottles. The compositions and the stability data presented below.

Composition (RNT-R5):

| Drug | 16.8 mg/ml |
| --- | --- |
| HPC | 50.0 mg/ml |
| Xylitol | 50.0 mg/ml |

-continued

| | |
|---|---|
| Sodium Saccharin | 3.0 mg/ml |
| MPS | 0.5 mg/ml |
| PPS | 0.05 mg/ml |
| pH | 5.55 |

TABLE 17

STABILITY AND IMPURITIES OF RNT-R5 AT 40° C.

| TIME (HRS) | ASSAY (%) | IMP. % | RRT | Imp name | pH |
|---|---|---|---|---|---|
| INITIAL | 100.0 | NOT DETECTED | | | 5.55 |
| 30 DAYS | 97.3 | 0.45 | 0.23 | UK | 5.65 |
| | | 0.26 | 0.45 | UK | |
| | | 0.08 | 0.53 | UK | |
| | | 0.37 | 0.82 | D | |
| | | 0.21 | 1.23 | UK | |
| TOTAL IMPURITIES | | 1.37 | | | |

Composition (RNT-R6):

| | |
|---|---|
| Drug | 16.8 mg/ml |
| HPC | 50.0 mg/ml |
| Xylitol | 50.0 mg/ml |
| Sodium Saccharin | 3.0 mg/ml |
| MPS | 0.5 mg/ml |
| PPS | 0.05 mg/ml |
| Pippermint | 0.001 mg/ml |
| pH | 5.81 |

TABLE 18

STABILITY AND IMPURITIES OF RNT-R6 AT 40° C.

| TIME (HRS) | ASSAY (%) | IMP. % | RRT | Imp name | pH |
|---|---|---|---|---|---|
| INITIAL | 100.0 | NOT DETECTED | | | 5.81 |
| 30 DAYS | 97.5 | 0.22 | 0.23 | UK | 6.15 |
| | | 0.13 | 0.45 | UK | |
| | | 0.05 | 0.53 | UK | |
| | | 0.09 | 0.82 | D | |
| | | 0.21 | 1.23 | UK | |
| | | 0.15 | 1.36 | UK | |
| TOTAL IMPURITIES | | 0.85 | | | |

EXAMPLE 12

Based on the stability data of the pilot batches, RNT-R2 had been chosen for further development. Several taste masking studies have been conducted; and it was found that the combination of RNT-R2 with raspberry flavor, orange flavor and peppermint flavor has provided a taste-masked formulation. The composition of the formulation is given below:

Composition of Flavored RNT-R2:

| | |
|---|---|
| Drug | 16.8 mg/ml |
| HPC | 50.0 mg/ml |
| Sodium Saccharin | 3.0 mg/ml |
| MPS | 0.7 mg/ml |

-continued

| | |
|---|---|
| PPS | 0.2 mg/ml |
| Pippermint flavor | 0.4% (v/v) |
| Orange flavor | 2.0% (v/v) |
| Raspberry flavor | 2.0% (v/v) |
| pH | 5.69 |

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

An alcohol-free aqueous pharmaceutical composition for oral administration comprising ranitidine and/or one or more physiologically acceptable salts thereof with a stabilizing effective amount of a cellulose, a starch, or a saccharide, wherein the composition has a pH in the range of about 4.85 to about 7.99.

What is claimed is:

1. An alcohol-free aqueous pharmaceutical composition for oral administration comprising ranitidine or a physiologically acceptable salt thereof, and about 1-5% (weight/volume) hydroxyethyl starch as a stabilizer, wherein the composition has a pH in the range of about 4.85 to about 7.99.

2. The composition of claim 1, containing about 5% of the stabilizer.

3. The composition of claim 1, wherein the pH is about 5.5 to 7.5.

4. The composition of claim 1, wherein the pH is obtained without the use of buffer salts.

5. The composition of claim 1, wherein the ranitidine concentration is about 16.8 milligrams per milliliter dose.

6. The composition of claim 1, further comprising a sweetening agent, a buffer, or a flavoring agent.

7. The composition of claim 6, wherein the sweetening agent is saccharin.

8. The composition of claim 6, wherein the flavoring agent is selected from the group consisting of peppermint, orange, raspberry, and combinations thereof.

9. The composition of claim 6, wherein the buffer comprises acetate, citrate, phosphate, succinate, or a pharmaceutically acceptable acid or base with pKa of about 4.5 to 6.5.

10. The composition of claim 6, further comprising methyl paraben sodium or propyl paraben sodium.

11. The composition of claim 10, wherein the concentration of methyl paraben sodium is about 0.7 mg/mL and the concentration of propyl paraben sodium is about 0.2 mg/mL.

12. The composition of claim 1, wherein the composition is at least 95% stable after 90 days at 40° C.

13. A method for stabilizing an aqueous alcohol-free ranitidine solution comprising the steps of:
a) providing the aqueous solution of alcohol-free ranitidine or of a salt thereof;
b) adding to the aqueous solution about 1-5% hydroxyethyl starch as a stabilizer; and
c) adjusting the pH to about 4.85 to about 7.99.

14. The method of claim 13, wherein about 5% of the stabilizer is added to the aqueous solution.

15. The method of claim 13, wherein the pH is about 5.5 to 7.5.

16. The method of claim 13, wherein the pH is obtained without the use of buffer salts.

17. The method of claim 13, wherein the final ranitidine concentration is about 16.8 mg per mL dose.

18. The method of claim 13, further comprising the step of adding a sweetening agent, a buffer, or a flavoring agent.

19. The method of claim 18, wherein the sweetening agent is saccharin.

20. The method of claim 18, wherein the flavoring agent is selected from the group consisting of peppermint, orange, raspberry, and combinations thereof.

* * * * *